United States Patent
Gooβen et al.

(10) Patent No.: US 9,120,736 B2
(45) Date of Patent: Sep. 1, 2015

(54) METHOD FOR PRODUCING UNSATURATED COMPOUNDS

(75) Inventors: Lukas J. Gooβen, Kaiserslautern (DE); Dominik Ohlmann, Namborn-Roschberg (DE); Markus Dierker, Düsseldorf (DE)

(73) Assignee: Cognis IP Management GmbH, Duesseldorf (DE)

( * ) Notice: Subject to any disclaimer, the term of this patent is extended or adjusted under 35 U.S.C. 154(b) by 1 day.

(21) Appl. No.: 14/112,454

(22) PCT Filed: Feb. 25, 2012

(86) PCT No.: PCT/EP2012/000823
§ 371 (c)(1),
(2), (4) Date: Oct. 17, 2013

(87) PCT Pub. No.: WO2012/143067
PCT Pub. Date: Oct. 26, 2012

(65) Prior Publication Data
US 2014/0046081 A1    Feb. 13, 2014

(30) Foreign Application Priority Data
Apr. 20, 2011   (EP) ..................................... 11003305

(51) Int. Cl.
| | | |
|---|---|---|
| *C07C 51/353* | (2006.01) | |
| *B01J 31/22* | (2006.01) | |
| *B01J 31/24* | (2006.01) | |
| *C07C 67/333* | (2006.01) | |
| *C07C 67/475* | (2006.01) | |
| *C11C 3/00* | (2006.01) | |
| *C10L 1/02* | (2006.01) | |

(52) U.S. Cl.
CPC ........... *C07C 51/353* (2013.01); *B01J 31/2217* (2013.01); *B01J 31/2273* (2013.01); *B01J 31/2278* (2013.01); *B01J 31/24* (2013.01); *C07C 67/333* (2013.01); *C07C 67/475* (2013.01); *C10L 1/026* (2013.01); *C11C 3/00* (2013.01); *B01J 2231/52* (2013.01); *B01J 2231/543* (2013.01); *B01J 2531/0216* (2013.01); *B01J 2531/821* (2013.01); *B01J 2531/824* (2013.01); *C07C 2531/24* (2013.01); *C10G 2300/1011* (2013.01)

(58) Field of Classification Search
None
See application file for complete search history.

(56) References Cited

U.S. PATENT DOCUMENTS

| | | | |
|---|---|---|---|
| 2005/0043574 A1* | 2/2005 | Powers et al. | 585/324 |
| 2007/0270621 A1* | 11/2007 | Millis et al. | 585/253 |
| 2010/0056839 A1* | 3/2010 | Ramachandran et al. | 585/646 |
| 2011/0021858 A1* | 1/2011 | Ramachandran et al. | 585/670 |
| 2011/0171147 A1 | 7/2011 | Samorski et al. | |

FOREIGN PATENT DOCUMENTS

WO   WO-2010/020368   2/2010

OTHER PUBLICATIONS

Sworen, J.C., et al., Competing ruthenium catalyzed metathesis condensation and isomerizatin of allylic olefins, 2003, Journal of molecular catalysis, A. Chemical, vol. 194, pp. 69-78.*
Schmidt, B., Connecting catalytic cycles by organometallic transformatins in situ: Novel prespectives in olefin metathesis field, Pure. Appl. Chem., vol. 78, No. 2, pp. 469-476.*
Haley, M., Tandem Reactions in organic synthesis: Ruthenium and Palladium Catalysis, 2006, Crimmins Group, 50 pages.*

* cited by examiner

*Primary Examiner* — Yate K Cutliff
(74) *Attorney, Agent, or Firm* — Servilla Whitney LLC

(57) ABSTRACT

The invention relates to a method for producing compositions containing unsaturated compounds, wherein (A) one or more unsaturated monocarboxylic acids having 10 to 24 C-atoms or esters of said monocarboxylic acids and optionally (B) one or more compounds having at least one C=C double bond (wherein the compounds (B) are different from the compounds (A)) are subjected to a tandem isomerization/metathesis reaction sequence in the presence of a palladium catalyst and a ruthenium catalyst, providing that the palladium catalysts used are compounds that contain at least one structural element Pd—P($R^1R^2R^3$), wherein the radicals $R^1$ to $R^3$, independently of one another, each comprise 2 to 10 C-atoms, which may be aliphatic, alicyclic, aromatic or heterocyclic respectively, providing that at least one of the radicals $R^1$ to $R^3$ contains a beta-hydrogen, wherein the palladium catalyst is used as such or is produced in situ, providing that the method is carried out in the absence of substances that have a pKa value of 3 or less.

9 Claims, No Drawings

METHOD FOR PRODUCING UNSATURATED COMPOUNDS

CROSS-REFERENCE TO RELATED APPLICATIONS

This application is the national stage entry of PCT/EP2012/000823, filed on Feb. 25, 2012, which claims priority to European Patent application number 11003305.7, filed on Apr. 20, 2011, both of which are incorporated herein by reference in their entireties.

FIELD

The present invention relates to a process for preparing unsaturated compounds. This process is a tandem isomerization/metathesis wherein a catalyst system comprising firstly a specific palladium catalyst and secondly a ruthenium catalyst is used.

BACKGROUND

Processes for preparing unsaturated alpha,omega-dicarboxylic diesters proceeding from unsaturated carboxylic acids are described in the prior art. Ngo et al. (JAOCS, Vol. 83, No. 7, p. 629-634, 2006) describes the metathesis of unsaturated carboxylic acids with the aid of first and second generation Grubbs catalysts.

WO 2010/020368 describes a process for preparing unsaturated alpha,omega-dicarboxylic acids and alpha,omega-dicarboxylic diesters, in which unsaturated carboxylic acids and/or esters of unsaturated carboxylic acids are converted in the presence of two specific ruthenium catalysts.

SUMMARY

An object of the present invention is to provide a novel process which enables the production of unsaturated compounds (which is understood to mean compounds with C═C double bonds) from unsaturated monocarboxylic acids and esters of such monocarboxylic acids.

DETAILED DESCRIPTION

The present invention provides a process for preparing compositions comprising unsaturated compounds, wherein (A) one or more unsaturated monocarboxylic acids having 10 to 24 carbon atoms or esters of these monocarboxylic acids and optionally (B) one or more compounds having at least one C═C double bond (the compounds (B) being different from the compounds (A)) are subjected to a tandem isomerization/metathesis reaction in the presence of a palladium catalyst and of a ruthenium catalyst, with the proviso that the palladium catalysts used are compounds which contain at least one structural element Pd—P($R^1R^2R^3$) where the $R^1$ to $R^3$ radicals each independently have 2 to 10 carbon atoms, each of which may be aliphatic, alicyclic, aromatic or heterocyclic, with the proviso that at least one of the $R^1$ to $R^3$ radicals contains a beta-hydrogen, the palladium catalyst being used as such or generated in situ, with the proviso that the process is performed in the absence of substances having a pKa of 3 or less.

The process according to the invention is a tandem isomerization/metathesis and has numerous advantages:

The catalysts do not need any chemical activation of any kind. More particularly, the palladium catalyst, which brings about a C═C isomerization before and after the metathesis step, works by itself without needing to be activated, for instance, by protic solvents and/or strong acids (which is understood here to mean acids having a pKa of 3 or less).

Only moderate amounts of the bimetallic Pd/Ru catalyst system are required.

The catalyst system is such that the Pd catalysts (which bring about a C═C isomerization) and Ru catalysts (which bring about metathesis) present therein do not impair or inhibit the effects of each other, which is not a given.

The catalyst system does not only work when the compounds (A) used are compounds having exclusively one C═C double bond, but it is also possible for several C═C double bonds to be present. This too is not a given. In operating practice, this is a great advantage, for instance, when the compound (A) used is oleic acid. In that case, it is not necessary that this oleic acid has an extremely high purity; instead, it is also possible to use oleic acid of technical-grade quality, for instance one containing approximately 80% oleic acid and 20% linoleic acid.

The catalyst system suppresses the formation of lactones (which are to be expected per se when, for example, unsaturated fatty acids such as oleic acid are admixed with an isomerization catalyst.

The process according to the invention can also be employed when the compounds (B) used are functionalized olefins (for instance olefins with the following functional groups: COOR, OH, OR, C═C, halogen, CN, where R is an alkyl group).

The process according to the invention can be performed without solvent if desired.

The process according to the invention requires only very mild temperatures.

The Reactants

The Reactants (A)

The reactants (A) are obligatory for the process according to the invention. The compounds (A) are unsaturated monocarboxylic acids having 10 to 24 carbon atoms or esters of these monocarboxylic acids. The monocarboxylic acids may optionally be branched. The C═C double bonds of the monocarboxylic acids may be present either in cis or in trans configuration. It is possible for one or more C═C double bonds to be present.

The unsaturated monocarboxylic acids (A) used are preferably compounds of the formula $R^1$—COOH where the $R^1$ radical comprises 9 to 23 carbon atoms. The $R^1$ radical may be cyclic or acyclic (noncyclic); the $R^1$ radical is preferably acyclic, and it may be branched or unbranched. Monocarboxylic acids having an unbranched $R^1$ radical are preferred.

The following brief notation is used to describe the unsaturated monocarboxylic acids: the first number describes the total number of carbon atoms in the monocarboxylic acids, the second number the number of double bonds and the number in brackets the position of the double bond in relation to the carboxyl group. Thus, the brief notation for oleic acid is 18:1 (9). When the double bond is in the trans configuration, this is represented by the abbreviation "tr". Thus, the brief notation for elaidic acid is 18:1 (tr9).

Suitable monounsaturated monocarboxylic acids are, for example, myristoleic acid [14:1 (9), (9Z)-tetradeca-9-enoic acid], palmitoleic acid [16:1 (9); (9Z)-hexadeca-9-enoic acid], petroselic acid [(6Z)-octadeca-6-enoic acid], oleic acid

[18:1 (9); (9Z)-octadeca-9-enoic acid], elaidic acid [18:1 (tr9); (9E)-octadeca-9-enoic acid)], vaccenic acid [18:1 (tr11); (11E)-octadeca-11-enoic acid], gadoleic acid [20:1 (9); (9Z)-eicosa-9-enoic acid], eicosenoic acid (=gondoic acid) [20:1 (11); (11Z)-eicosa-11-enoic acid], cetoleic acid [22:1 (11); (11Z)-docosa-11-enoic acid], erucic acid [22:1 (13); (13Z)-docosa-13-enoic acid], nervonic acid [24:1 (15); (15Z)-tetracosa-15-enoic acid]. Additionally suitable are functionalized monounsaturated monocarboxylic acids, for instance ricinoleic acid, furan fatty acids, methoxy fatty acids, keto fatty acids and epoxy fatty acids such as vernolic acid (cis-12,13-epoxyoctadec-cis-9-enoic acid), and finally also branched monocarboxylic acids such as phytanoic acid.

Suitable polyunsaturated monocarboxylic acids are, for example, linoleic acids [18:2 (9,12); (9Z,12Z)-octadeca-9, 12-dienoic acid], alpha-linolenic acid [18:3 (9,12,15); (9Z, 12Z,15Z)-octadeca-9,12,15-trienoic acid], gamma-linolenic acid [18:3 (6,9,12); (6Z,9Z,12Z)-octadeca-6,9,12-trienoic acid], calendic acid [18:3 (8,10,12); (8E,10E,12Z)-octadeca-8,10,12-trienoic acid], punicic acid [18:3 (9,11,13); (9Z,11E, 13Z)-octadeca-9,11,13-trienoic acid], alpha-eleostearic acid [18:3 (9,11,13); (9Z,11E,13E)-octadeca-9,11,13-trienoic acid], arachidonic acid [20:4 (5,8,11,14), (5Z,8Z,11Z,14Z)-eicosa-5,8,11,14-tetra-enoic acid], timnodonic acid [20:5 (5,8,11,14,17), (5Z,8Z,11Z,14Z,17Z)-eicosa-5,8,11,14,17-pentaenoic acid], clupanodonic acid [22:5 (7,10,13,16,19), (7Z,10Z,13Z,16Z,19Z)-docosa-7,10,13,16,19-pentaenoic acid], cervonic acid [22:6 (4,7,10,13,16,19), (4Z,7Z,10Z, 13Z,16Z,19Z)-docosa-4,7,10,13,16,19-hexa-enoic acid].

Suitable reactants (A) are additionally esters of the mono- or polyunsaturated monocarboxylic acids mentioned. Suitable esters are especially esters of these monocarboxylic acids with alcohols $R^2$—OH where $R^2$ is an alkyl radical having 1 to 8 carbon atoms. Examples of suitable $R^2$ radicals include: methyl, ethyl, propyl, isopropyl, butyl, 2-methylpropyl, pentyl, 2,2-dimethylpropyl, 2-methylbutyl, 3-methylbutyl, hexyl, 1-methylpentyl, 2-methylpentyl, 3-methylpentyl, 4-methylpentyl, 1-ethylbutyl, 2-ethylbutyl, heptyl and octyl radicals.

Suitable reactants (A) are additionally esters of the mono- or polyunsaturated monocarboxylic acids mentioned with glycerol (=glyceryl esters). In this case, glyceryl monoesters (=monoglycerides, monoacyl-glycerol), glyceryl diesters (=diglycerides, diacyl-glycerol) and glyceryl triesters (=triglycerides, triacylglycerol), and also mixtures of these different glyceryl esters, are suitable.

The unsaturated monocarboxylic acids or the esters of the unsaturated monocarboxylic acids may be present either individually or in mixtures with one another. While exclusively one unsaturated monocarboxylic acid or the ester of only one unsaturated monocarboxylic acid is used, the reaction which takes place in the context of the process according to the invention is one which can be classified as an isomerizing self-metathesis. When different unsaturated monocarboxylic acids or esters of different unsaturated monocarboxylic acids are used, the reaction which takes place in the context of the process according to the invention is one which can be classified as an isomerizing cross-metathesis.

In a preferred embodiment of the invention, monounsaturated monocarboxylic acids and/or esters of monounsaturated monocarboxylic acids and/or mixtures of the monounsaturated monocarboxylic acids or mixtures of the esters of monounsaturated monocarboxylic acids are used.

When, in the context of the process according to the invention, exclusively the reactants (A) are used, the metathesis step of the tandem isomerization/metathesis reaction is a homo- or self-metathesis.

The Reactants (B)

The reactants (B) are optional for the process according to the invention. The reactants (B) are different from the reactants (A) and contain at least one C=C double bond per molecule. The reactants (B) preferably contain 2 to 24 carbon atoms per molecule.

The compounds (B) may contain further functional groups which are inert under the reaction conditions. Examples of such functional groups are, for instance, COOR, OH, OR, C=C, halogen and CN, where R is an alkyl group.

Examples of suitable reactants (B) are especially unsaturated dicarboxylic acid derivatives (for example maleic esters), and also mono-, di- or polyolefins having 2-20 carbon atoms (which may be linear, branched, alicyclic or aromatic), for instance 1-hexene or styrene.

When, in the context of the process according to the invention, one or more reactants (B) are also used in addition to the obligatory reactants (A), the metathesis step of the tandem isomerization/metathesis reaction is a cross-metathesis, and the special case of what is called an ethenolysis is present when (B) is ethene ($CH_2=CH_2$).

If, in the context of the process according to the invention, one or more reactants (B) are also used in addition to the obligatory reactants (A), the molar ratio of (A):(B) is preferably set to a value in the range from 1:0.05 to 1:5.

In the specific case that the reactant (B) used is ethylene, it is preferable to work at a partial pressure of ethylene in the range between 1 and 50 bar and especially 1 to 10 bar.

The Catalysts

The process according to the invention is performed in the presence of a specific palladium catalyst and a ruthenium catalyst.

The Palladium Catalyst

The palladium catalysts used are compounds which contain at least one structural element Pd—P ($R^1R^2R^3$) where the $R^1$ to $R^3$ radicals each independently have 2 to carbon atoms, each of which may be aliphatic, alicyclic, aromatic or heterocyclic, with the proviso that at least one of the $R^1$ to $R^3$ radicals contains a beta-hydrogen, the palladium catalyst being used as such or generated in situ.

Aliphatic radicals may be linear or branched; they may also be in cyclic form; the structural elements mentioned may also be present in combination. Aromatic radicals may also have alkyl substituents. A beta-hydrogen is present when the Pd—P—C—C—H arrangement is present in the palladium catalyst.

As explained above, the palladium catalyst is used as such or generated in situ.

It is explicitly emphasized that the palladium catalysts for use in accordance with the invention work by themselves, which is understood to mean that they do not require a chemical activation by an additional activating substance.

The palladium catalysts may be mono- or polynuclear.

In one embodiment, palladium catalysts containing two palladium atoms per molecule are used.

In one embodiment, palladium catalysts containing two palladium atoms per molecule are used, where the two palladium atoms are joined to one another via a spacer X.

Therefore, these palladium catalysts contain the structural element Pd—X—Pd.

The nature of the spacer is not subject to any restriction per se. Suitable spacers X are, for example, halogen, oxygen, O-alkyl, sulfur, sulfur-alkyl, disubstituted nitrogen, carbon monoxide, nitrile, diolefin.

In a preferred embodiment, the palladium catalysts used are the compounds (I)

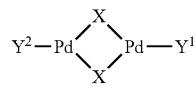
(I)

in which: X is a spacer selected from halogen, oxygen and O-alkyl, $Y^1$ is a $P(R^1R^2R^3)$ group in which $R^1$, $R^2$ and $R^3$ are each as defined above, $Y^2$ is a $P(R^4R^5R^6)$ group in which $R^4$, $R^5$ and $R^6$ each independently have 2 to 10 carbon atoms, each of which may be aliphatic, alicyclic, aromatic or heterocyclic.

It follows from this definition that the compounds (I) contain at least one beta-hydrogen in the structural element Pd—Y1 (owing to the $R^1$ to $R^3$ radicals present therein). In the structural element Pd—Y2, a beta-hydrogen need not necessarily be present.

Particular preference is given to those compounds (I) in which the spacer is halogen and especially bromine. Very particular preference is given to those compounds (I) in which the spacer is bromine and the $R^1$, $R^2$ and $R^3$ radicals are each defined as tert-butyl.

In a preferred embodiment, the palladium catalysts used are the compounds (I-a)

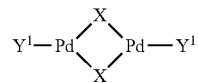
(I-a)

in which: X is a spacer selected from halogen, oxygen and O-alkyl, $Y^1$ is a $P(R^1R^2R^3)$ group in which $R^1$, $R^2$ and $R^3$ are each as defined above, $Y^2$ is a $P(R^4R^5R^6)$ group in which $R^4$, $R^5$ and $R^6$ each independently have 2 to 10 carbon atoms, each of which may be aliphatic, alicyclic, aromatic or heterocyclic.

Particular preference is given to those compounds (I-a) in which the spacer is halogen and especially bromine. Very particular preference is given to those compounds (I-a) in which the spacer is bromine and the $R^1$, $R^2$ and $R^3$ radicals are each defined as tert-butyl.

As already explained, the palladium catalyst is used as such or generated in situ. In situ generation can mean, for example, for a palladium catalyst of the (I) or (I-a) type, that a compound $L_3$-Pd—X—Pd-$L_3$ where L represents phosphine ligands without beta-hydrogen is used and converted by ligand exchange in situ to a compound (I) or (I-a).

In one embodiment, the palladium catalyst is a homogeneous catalyst.

In one embodiment, the palladium catalyst is a heterogeneous catalyst. In a specific embodiment, a palladium catalyst of the formula (I) is immobilized via the $Y^1$ and/or $Y^2$ group on a solid substrate or in an ionic liquid.

The palladium catalyst is preferably used in an amount in the range from 0.01 to 2.0 mol %—based on the amount of reactant (A) used; the range from 0.1 to 1.0 mol % is particularly preferred.

The Ruthenium Catalyst

The chemical nature of the ruthenium catalyst is not critical per se.

Examples of suitable ruthenium catalysts are:
Catalyst (II-a) with the following structural formula:

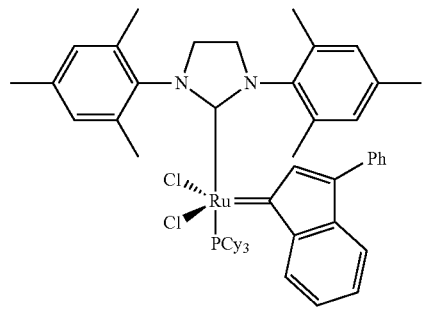

The chemical name for this catalyst is dichloro[1,3-bis(mesityl)-2-imidazolidinylidene]-(3-phenyl-1H-inden-1-ylidene)(tricyclohexylphosphine)ruthenium(II), CAS No. 536724-67-1. It is commercially available under the Neolyst™ M2 name from Umicore.

Catalyst (II-b) with the following structural formula:

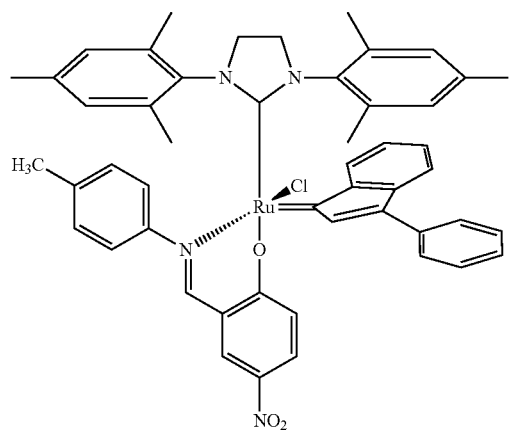

The chemical name for this catalyst is [1,3-bis(2,4,6-trimethylphenyl)-2-imidazolidinylidene]-[2-[[(4-methyl-phenyl)imino]methyl]-4-nitrophenolyl]-[3-phenyl-1H-inden-1-ylidene]ruthenium(II) chloride, CAS No. 934538-04-2. It is commercially available, for example, under the Neolyst™ M41 name from Umicore.

Catalyst (II-c) with the following structural formula:

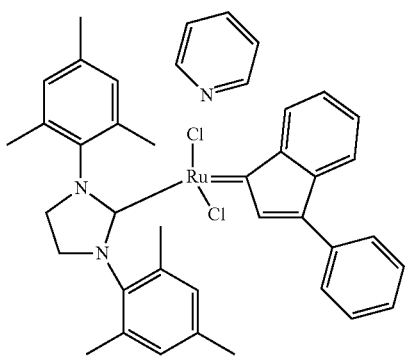

The chemical name for this catalyst is 3-bis(mesityl)-2-imidazolidinylidene]-[2-[[(2-methylphenyl)imino]-methyl]phenolyl]-[3-phenyl-1H-inden-1-ylidene]-ruthenium(II) chloride. CAS No. 1031262-76-6. It is commercially available, for example, under the Neolyst™ M31 name.

Catalyst (II-d) with the following structural formula:

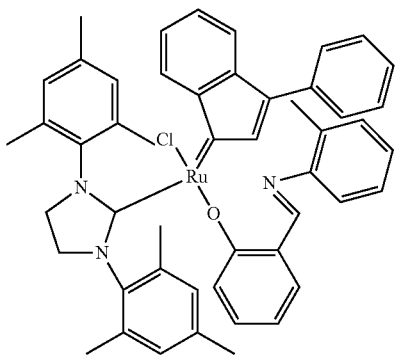

The chemical name for this catalyst is 3-bis(mesityl)-2-imidazolidinylidene]-[2-[[(2-methylphenyl)imino]-methyl]phenolyl]-[3-phenyl-1H-inden-1-ylidene]-ruthenium(II) chloride. CAS No. 934538-12-2. It is commercially available, for example, under the Neolyst™ M42 name from Umicore.

Catalyst (II-e) with the following structural formula:

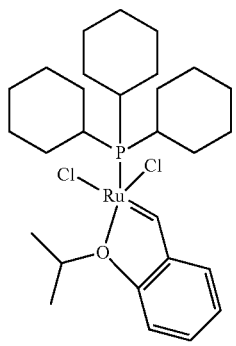

The chemical name for this catalyst is dichloro(o-isopropoxyphenylmethylene)(tricyclohexylphosphine)-ruthenium (II). CAS No. 203714-71-0. It is commercially available, for example, under the first generation Hoveyda-Grubbs catalyst name.

Catalyst (II-f) with the following structural formula:

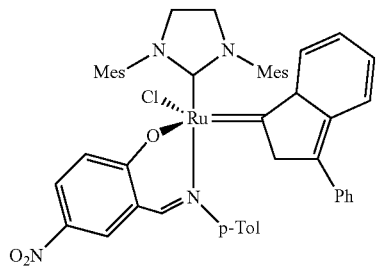

The chemical name for this catalyst is 1,3-bis(2,4,6-trimethylphenyl)-2-imidazolidinylidene-[2-[[(4-methyl-phenyl)imino]methyl]-4-nitrophenolyl]-[3-phenyl-1H-inden-1-ylidene]ruthenium(II)chloride. CAS No. 934538-04-2. It is commercially available, for example, under the Neolys™M41 name from Umicore.

Catalyst (II-g) with the following structural formula:

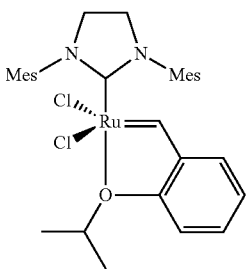

The chemical name for this catalyst is 1,3-bis(2,4,6-trimethylphenyl)-2-imidazolidinylidene)dichloro(o-iso-propoxyphenylmethylene)ruthenium(II). CAS No. 301224-40-8. It is commercially available, for example, under the second generation of Hoveyda-Grubbs catalyst name.

The ruthenium catalyst is preferably used in an amount in the range from 0.01 to 5 mol %—based on the amount of reactant (A) used; the range from 0.3 to 1.5 mol % is particularly preferred.

Reaction Conditions

Temperature

The process according to the invention is preferably performed at temperatures in the range from 25 to 90° C. and especially 40 to 80° C. A range from 50 to 70° C. is particularly preferred.

Solvent

The process can be performed in customary organic solvents in which the reactants (A) or the reactants (A) and (B) and the catalysts used—if the catalysts are used in the form of homogeneous catalysts—dissolve.

It should be stated explicitly that the compounds covered by the definition of the reactants (A) and (B) are not solvents in the context of the present invention, which means that solvents must be structurally different from the compounds (A) and (B). Preference is given to using aprotic solvents, for instance hydrocarbons (e.g. hexane or tetrahydrofuran).

In a further preferred embodiment of the invention, the process is performed without solvent.

Other Parameters

The reaction is preferably performed in the absence of acids having a pKa of 3 or less. Examples of acids having a pKa of 3 or less are, for instance, mineral acids, p-toluenesulfonic acid, methanesulfonic acid.

The process according to the invention is preferably performed in the absence of oxygen, for example in an inert gas stream (for example under nitrogen or argon or by means of passage of nitrogen or argon), or under reduced pressure. If desired, it is also possible for component (B) itself, if it is used and is present in the gaseous state under the reaction conditions, to serve as the inert gas.

Purification

The process according to the invention, which is an isomerizing metathesis (=a tandem isomerization/metathesis reaction), leads to substance mixtures whose complexity can be controlled by process parameters including the molar ratio of reactants A and B, nature of reactant B, partial pressure of a gaseous reactant B, reaction regime under reduced pressure, molar ratio of the catalysts, reaction time and temperature. If desired, the substance mixtures can be subjected to a separation by customary processes, for example by distillation, by fractional crystallization or by extraction.

It is optionally possible to subject products obtained by the process according to the invention to a hydrogenation or another cross-metathesis. The latter (another cross-metathesis) may be a desired option if conversion of the monocarboxylates present in the product mixture to dicarboxylates is desired.

Use

The mixtures of olefins, mono- and dicarboxylates obtainable in accordance with the invention from unsaturated fatty acids are similar as such to the fuel used under the name "metathesized biodiesel", but can if desired also be fractionated into a monoester fraction and a diester fraction, each of which have their own possible uses: monocarboxylate mixtures are suitable, for instance, for plastics applications, surfactants, hydraulic oils and lubricants. Unsaturated dicarboxylates cannot be obtained from mineral oil but play an important role for the production of odorants, adhesives and specialty antibiotics. At the same time, due to the double bond present, they enable further modifications, for example for novel biobased polyesters, polyamides, polyurethanes, resins, fibers, coatings and adhesives.

EXAMPLES

Substances Used

Catalyst (A) Compound of the structure (I-a) where X=Br and the $R^1$, $R^2$ and $R^3$ radicals are each defined as tert-butyl.
Catalyst (B1) Compound of the structure (II-c)
Catalyst (B2) Compound of the structure (II-d)
Catalyst (B3) Compound of the structure (II-e)
Catalyst (B4) Compound of the structure (II-f)
Catalyst (B5) Compound of the structure (II-g)
Pd(dba)$_2$ Bis(dibenzylideneacetone)palladium(0)
BDTBPB 1,2-Bis(di-t-butylphosphinomethyl)benzene
Umicore M11 Dichloro(3-phenyl-1H-inden-1-ylidene)bis(isobutylphobane)ruthenium(II)

Inventive Examples

Example 1

Isomerizing Self-metathesis of Oleic Acid

Reaction:
A 20 ml reaction vessel with beaded rim and stirrer bar was initially charged with catalyst (A) (1.2 mg, 1.5 µmol) and catalyst (B1) (2.3 mg, 3 µmol), and the vessel was closed with a septum and purged three times with argon. Hexane (0.5 ml) and oleic acid (90%, 1.5 mmol, 471 mg) were added by syringe and the mixture was stirred at 70° C. for 4 h.
Analysis:

After cooling to room temperature, methanol (2 ml) and conc. sulfuric acid (50 µl) were added by syringe and the mixture was stirred at 70° C. for 2 h. The GC of the mixture showed a $C_{10}$ to at least $C_{22}$ olefin fraction, unsaturated monoesters $C_{10}$ to at least $C_{26}$ and unsaturated diesters $C_{12}$ to at least $C_{22}$. Details can be found in Table 1.

TABLE 1

Product distribution in Example 1

| Fraction | Olefins (%)[a] | Monoesters (%)[a] | Diesters (%)[a] |
|---|---|---|---|
| C10 | —[b] | —[b] | — |
| C11 | 0.28 | 3.31[c] | —[b] |
| C12 | 0.54 | 3.83 | 0.17 |
| C13 | 0.91 | 4.03 (with C19 olefin) | 0.31 |
| C14 | 1.24 | 3.95 (with C20 olefin) | 1.15 |
| C15 | 2.03 | 4.30 (with C21 olefin) | 2.04 |
| C16 | 2.54 | 4.66 (with C22 olefin) | 3.32 |
| C17 | 3.31 | 5.62 (with C23 olefin) | 4.34 |
| C18 | 3.83[c] | 6.27[c] | 4.55[c] |
| C19 | 4.03 (with C13 monoester) | 6.65 | 4.48 |
| C20 | 3.95 (with C14 monoester) | 5.77 | 3.79[c] |
| C21 | 4.30 (with C15 monoester) | 4.31 | 2.75 |
| C22 | 4.66 (with C16 monoester) | 3.00[c] | 1.67 |
| C23 | 5.62 (with C17 monoester) | 1.68 | — |
| C24 | — | 1.08 | — |
| C25 | — | 0.59 | — |
| C26 | — | 0.19 | — |

[a] gas chromatography analysis. The contents of all double bond isomers of a particular chain length are reported in each case;
[b] relatively short chains not dissolved;
[c] comparison with authentic sample As evident from Table 1, in contrast to conventional metathesis reactions with fatty acids, a broad chain length distribution was obtained for each product compound class (olefins, monoesters and diesters) proceeding from a homogeneous compound. This distribution contains many compounds which are obtainable only with very great difficulty, if at all, by another route. Such biobased products have been found to be advantageous from an ecological point of view, for instance with the aid of life-cycle analysis.

Example 2

Isomerizing Cross-metathesis of Oleic Acid and Maleic Acid

Reaction: A 20 ml reaction vessel with beaded rim and stirrer bar was initially charged with catalyst (A) (5.8 mg, 7.5 µmol) and catalyst (B2) (12.7 mg, 15 µmol), and the vessel was closed with a septum and purged three times with argon. THF (3 ml) and oleic acid (90%, 1.0 mmol, 314 mg) were added by syringe and the mixture was stirred at 70° C. for 16 h.

Analysis: After esterification with methanol and sulfuric acid analogously to Example 1, the GC of the mixture showed unsaturated $C_7$ to $C_{22}$ monoesters and unsaturated $C_4$ to $C_{22}$ diesters. Details can be found in Table 2.

TABLE 2

Product distribution in Example 2

| Fraction | Monoesters (%)[a] | Diesters (%)[a] |
|---|---|---|
| C4 | — | 24.51[c] |
| C5 | — | 0.36 |
| C6 | —[b] | 0.92 |
| C7 | 0.24 | 3.77 |
| C8 | 0.6 | 0.94 |
| C9 | 1.17 | 2.68 (with C14 monoester) |
| C10 | 1.73 | |
| C11 | 2.67 | 3.77 |
| C12 | 3.32 | 4.22 |
| C13 | 2.84 | 0.92 |
| C14 | 2.68 (with C9 diester) | 0.33 |
| C15 | 2.37 | 0.58 |
| C16 | 3.49 | 1.22 |
| C17 | 5.07 | 2.23 |
| C18 | 6.17 | 3.58 |
| C19 | 4.97 | 2.74 |
| C20 | 3.09 | 1.12 |
| C21 | 1.46 | 1.00 |
| C22 | 0.81 | 0.33 |
| C23 | — | — |

[a] gas chromatography analysis. The contents of all double bond isomers of a particular chain length are reported in each case;
[b] relatively short chains not dissolved;
[c] principally from starting material (B) maleic acid The reaction according to Example 2 for the first time opens up access to product mixtures composed of mono- and dicarboxylates with broad chain length distribution. Such a mixture can be achieved only by the tandem reaction of isomerizing cross-metathesis described herein, and not by sequential isomerization-cross-metathesis or cross-metathesis-isomerization. The reaction according to Example 2 is an example for a wide range of isomerizing cross-metathesis reactions in which one or more reactants (A) and reactants (B) can be used.

Example 3

Isomerizing Self-metathesis of Oleic Acid with Catalyst B1

Reaction: A 20 ml reaction vessel with beaded rim and stirrer bar was initially charged with catalyst (A) (11 mg, 14.2 µmol) and catalyst (B1) (11 mg, 15 µmol), and the vessel was closed with a septum and purged three times with argon. Oleic acid (90%, 3 mmol, 942 mg) was added by syringe and the mixture was stirred at 70° C. for 20 h.

Analysis: After esterification with methanol and sulfuric acid analogously to Example 1, the GC of the mixture showed a broad distribution as in Table 1.

Example 4

Isomerizing Self-metathesis of Methyl Oleate with Catalyst B1

Reaction: A 20 ml reaction vessel with beaded rim and stirrer bar was initially charged with catalyst (A) (5.8 mg, 7.5 µmol) and catalyst (B1) (9.4 mg, 12.5 µmol), and the vessel was closed with a septum and purged three times with argon. Methyl oleate (90%, 2.66 mmol, 876 mg) was added by syringe and the mixture was stirred at 70° C. for 20 h.

Analysis: The GC of the mixture exhibited a broad distribution as in Table 1.

Example 5

Isomerizing Self-metathesis of Oleic Acid with Catalyst B2

Reaction: A 20 ml reaction vessel with beaded rim and stirrer bar was initially charged with catalyst (A) (7 mg, 9 µmol) and catalyst (B2) (12.7 mg, 15 µmol), and the vessel was closed with a septum and purged three times with argon. Oleic acid (90%, 3 mmol, 942 mg) was added by syringe and the mixture was stirred at 70° C. for 20 h.

Analysis: After esterification with methanol and sulfuric acid analogously to Example 1, the GC of the mixture showed a broad distribution as in Table 1.

Example 6

Isomerizing Self-metathesis of Methyl Oleate with Catalyst B2

Reaction: A 20 ml reaction vessel with beaded rim and stirrer bar was initially charged with catalyst (A) (5.8 mg, 7.5 µmol) and catalyst (B2) (10.5 mg, 12.5 µmol), and the vessel was closed with a septum and purged three times with argon. Methyl oleate (90%, 2.66 mmol, 876 mg) was added by syringe and the mixture was stirred at 70° C. for 20 h.

Analysis: The GC of the mixture exhibited a broad distribution as in Table 1.

Example 7

Isomerizing Self-metathesis of Methyl Oleate with Catalyst B3

Reaction: A 20 ml reaction vessel with beaded rim and stirrer bar was initially charged with catalyst (A) (5.8 mg, 7.5 µmol) and catalyst (B3) (7.6 mg, 12.5 µmol), and the vessel was closed with a septum and purged three times with argon. Methyl oleate (90%, 2.66 mmol, 876 mg) was added by syringe and the mixture was stirred at 70° C. for 20 h.

Analysis: The GC of the mixture exhibited a broad distribution as in Table 1.

Example 8

Isomerizing Ethenolysis of Oleic Acid

Reaction: A 20 ml reaction vessel with beaded rim and stirrer bar was initially charged with catalyst (A) (3.07 mg, 3.8 µmol, 0.0075 equiv.) and catalyst (B4) (6.66 mg, 7.5 µmol, 0.015 equiv.), and the vessel was sealed with a septum and purged three times with ethylene (N30 purity, 1 bar). Hexane (3.0 ml) and oleic acid (99%, 0.5 mmol, 143 mg) were added by syringe and the mixture was stirred at 50° C. for 16 h.

Analysis: After cooling to room temperature, methanol (2 ml) and conc. sulfuric acid (50 µl) were added by syringe and the mixture was stirred at 70° C. for 2 h. The GC of the mixture showed full conversion of the fatty acid to a mixture of olefins and unsaturated mono- and diesters, of which the olefin fraction has been analyzed in detail by way of example. After cooling, the olefin fraction was removed by admixing the reaction mixture with methanol (2.0 ml), water (0.6 ml) and powdered NaOH (200 mg). This mixture was stirred at 80° C. under ethylene pressure 1 bar for 4 h.

Extraction with hexane and filtration through basic alumina were followed by analysis by GC. This resulted in the chain length distribution of the olefins reported in 3.

TABLE 3

Chain length distribution of the olefin fraction in Example 8

| Chain length | Area % | Rel. area % |
|---|---|---|
| C7* | 8.610 | 13.51 |
| C8 | 9.411 | 14.77 |
| C9 | 9.861 | 15.47 |
| C10 | 9.590 | 15.05 |
| C11 | 8.051 | 12.63 |
| C12 | 5.467 | 8.58 |
| C13 | 3.923 | 6.16 |
| C14 | 2.689 | 4.22 |
| C15 | 1.904 | 2.99 |
| C16 | 1.500 | 2.35 |
| C17 | 1.037 | 1.63 |
| C18 | 0.839 | 1.32 |
| C19 | 0.474 | 0.74 |
| C20 | 0.201 | 0.32 |
| C21 | 0.116 | 0.18 |
| C22 | 0.056 | 0.09 |
| C23 | — | — |

*C6 fraction unresolved because of overlapping signals.

As is apparent from Table 3, in contrast to the isomerizing self-metathesis of oleic acid, an olefin fraction with distinctly shortened chain lengths was obtained. Especially short- and mid-chain olefins as otherwise obtainable only from petrochemical distillates are obtainable from fatty acids in this way. The majority of the carbon atoms in the product mixture originates from renewable sources, as a result of which the process can constitute an alternative to ethylene oligomerization by means of SHOP processes.

Example 9

Isomerizing Cross-metathesis of Oleic Acid and (E)-3-Hexenedioic Acid

Reaction: A 20 ml reaction vessel with beaded rim and stirrer bar was initially charged with (E)-3-hexenedioic acid (73.5 mg, 0.50 mmol, 2.0 equiv.), catalyst (A) (5.1 mg, 6.3 µmol, 0.025 equiv.), and catalyst (B5) (7.9 mg), 12.5 µmol, 0.05 equiv.), and the vessel was closed with a septum and purged three times with argon. THF (1.0 ml) and oleic acid (99%, 0.25 mmol, 71.3 mg) were added by syringe, and the mixture was stirred at 60° C. for 16 h.

Analysis: After cooling to room temperature, methanol (2 ml) and conc. sulfuric acid (50 µl) were added by syringe and the mixture was stirred at 70° C. for 2 h. The GC of the mixture showed full conversion of the two carboxylic acids to a mixture of olefins and unsaturated mono- and diesters, of which the olefin fraction was analyzed in detail by way of example. The olefin fraction was removed after cooling, by admixing the reaction mixture with methanol (2.0 ml), water (0.6 ml) and powdered NaOH (200 mg). This mixture was stirred at 80° C. for 4 h. Extraction with hexane and filtration through basic alumina were followed by analysis by GC. This resulted in the chain length distribution of the olefins reported in 4, as a representative example of the complex analysis of the overall mixture.

TABLE 4

Chain length distribution of the olefin fraction in Example 9

| Chain length | Area % | Rel. area % |
|---|---|---|
| C7 | 0.008 | 8.54 |
| C8 | 0.011 | 11.76 |
| C9 | 0.011 | 11.63 |
| C10 | 0.011 | 10.94 |
| C11 | 0.010 | 10.33 |
| C12 | 0.009 | 9.32 |
| C13 | 0.007 | 6.76 |
| C14 | 0.008 | 8.08 |
| C15 | 0.006 | 6.03 |
| C16 | 0.004 | 4.61 |
| C17 | 0.004 | 3.98 |
| C18 | 0.003 | 2.85 |
| C19 | 0.002 | 2.07 |
| C20 | 0.002 | 1.72 |
| C21 | 0.001 | 1.37 |
| C22 | — | — |

COMPARATIVE EXAMPLES

Comparative Example 1

Reaction: A 20 ml reaction vessel with beaded rim and stirrer bar was initially charged with Pd(dba)$_2$ (7.19 mg, 12.5 µmol), BDTBPB (24.7 mg, 6.25 µmol) and catalyst (B3) (7.6 mg, 12.5 µmol), and the vessel was sealed with a septum and purged three times with argon. Oleic acid (90%, 2.83 mmol, 887 mg) was added by syringe and the mixture was stirred at 70° C. for 20 h.

Analysis: After esterification with methanol and sulfuric acid analogously to Example 1, the GC of the mixture showed only traces of self-metathesis products (3% octadec-9-ene, 4% dimethyl 1,18-octadec-9-enoate); the rest is divided between C18:1 double bond isomers of methyl oleate.

Assessment/comment: The reaction of Comparative Example 1 showed only isomerization activity, but olefin metathesis was almost completely inhibited. No broad and balanced product distribution as in Example 1 was achieved.

Comparative Example 2

Reaction: A 20 ml reaction vessel with beaded rim and stirrer bar was initially charged with Pd(dba)$_2$ (2 mg, 5 mmol), BDTBPB (24.7 mg, 6.25 µmol) and catalyst (B2) (10.5 mg, 12.5 µmol), and the vessel was sealed with a septum and purged three times with argon. Oleic acid (90%, 2.83 mmol, 887 mg) was added by syringe and the mixture was stirred at 70° C. for 20 h.

Analysis: After esterification with methanol and sulfuric acid analogously to Example 1, the GC of the mixture showed dominant proportions of self-metathesis products (18% octadec-9-ene, 21% dimethyl 1,18-octadec-9-enoate) and unisomerized starting material (31% methyl oleate). The rest was divided between C18:1 double bond isomers of methyl oleate and traces (<0.5%) of metathesis products with other chain lengths.

Assessment/Comment: The reaction of Comparative Example 2 showed only metathesis activity, but the isomerization was almost completely inhibited. No broad and balanced product distribution as in Example 1 was achieved.

Comparative Example 3

Reaction: A 20 ml reaction vessel with beaded rim and stirrer bar was initially charged with Pd(dba)$_2$ (2 mg, 5 µmol), BDTBPB (24.7 mg, 6.25 μmol) and catalyst (Umicore M11) (9.5 mg, 12.5 μmol), and the vessel was sealed with a septum and purged three times with argon. Oleic acid (90%, 2.83 mmol, 887 mg) was added by syringe and the mixture was stirred at 70° C. for 20 h.

Analysis: After esterification with methanol and sulfuric acid analogously to Example 1, the GC of the mixture showed only small proportions of self-metathesis products (3% octadec-9-ene, 4% dimethyl 1,18-octadec-9-enoate). Approx. 80% of C18:1 double bond isomers of methyl oleate were present. Products of other chain lengths were detected only in traces (<0.3%).

Assessment/comment: The reaction of Comparative Example 3 showed only isomerization activity, but olefin metathesis was almost completely inhibited. No broad and balanced product distribution as in Example 1 was achieved.

Comparative Example 4

Reaction: A 20 ml reaction vessel with beaded rim and stirrer bar was initially charged with Pd(dba)$_2$ (7.19 mg, 12.5 μmol), BDTBPB (24.7 mg, 6.25 μmol) and catalyst (B2) (10.5 mg, 12.5 μmol), and the vessel was sealed with a septum and purged three times with argon. Methyl oleate (90%, 2.66 mmol, 876 mg) was added by syringe and the mixture was stirred at 70° C. for 20 h.

Analysis: The GC of the mixture showed dominant proportions of self-metathesis products (24% octadec-9-ene, 24% dimethyl 1,18-octadec-9-enoate) and 33% unisomerized starting material (methyl oleate). Products of other chain lengths were present only in traces (<0.3%).

Assessment/comment: The reaction of Comparative Example 4 showed only metathesis activity, but the isomerization was almost completely inhibited. No broad and balanced product distribution as in Example 1 was achieved.

Comparative Example 5

Reaction: A 20 ml reaction vessel with beaded rim and stirrer bar was initially charged with Pd(dba)$_2$ (7.19 mg, 12.5 μmol), BDTBPB (24.7 mg, 6.25 μmol) and catalyst (B1) (9.4 mg, 12.5 μmol), and the vessel was sealed with a septum and purged three times with argon. Methyl oleate (90%, 2.66 mmol, 876 mg) was added by syringe and the mixture was stirred at 70° C. for 20 h.

Analysis: The GC of the mixture showed dominant proportions of self-metathesis products (30% octadec-9-ene, 30% dimethyl 1,18-octadec-9-enoate) and 23% unisomerized starting material (methyl oleate). Products of other chain lengths were present only in traces (<0.3%).

Assessment/comment: The reaction of Comparative Example 5 showed only metathesis activity, but the isomerization was almost completely inhibited. No broad and balanced product distribution as in Example 1 was achieved.

The invention claimed is:

1. A process for preparing compositions comprising unsaturated compounds, wherein (A) one or more unsaturated monocarboxylic acids having 10 to 24 carbon atoms or esters of these monocarboxylic acids are subjected to a tandem isomerization/metathesis reaction in the presence of a palladium catalyst and of a ruthenium catalyst, with the proviso that the palladium catalyst is a compound of formula (I-a):

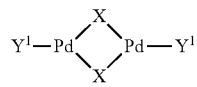

(I-a)

in which the spacer X is bromine and $Y^1$ is a $P(R^1R^2R^3)$ wherein the $R^1$, $R^2$ and $R^3$ radicals are each defined as tert-butyl, the palladium catalyst being used as such or generated in situ, with the proviso that the process is performed in the absence of substances having a pKa of 3 or less.

2. The process of claim 1, wherein the palladium catalyst is a homogeneous catalyst.

3. The process of claim 1, wherein the palladium catalyst is a heterogeneous catalyst.

4. The process of claim 1, wherein the reaction is performed in an aprotic solvent.

5. The process of claim 1, wherein the reaction is performed in the absence of a solvent.

6. The process of claim 1, wherein the reaction is performed in the absence of acids.

7. The process of claim 1, wherein the reaction is performed in the absence of oxygen.

8. The process of claim 1, wherein the compound (A) is selected from the group consisting of the unsaturated carboxylic acids having 14 to 24 carbon atoms and the esters of unsaturated carboxylic acids having 14 to 24 carbon atoms.

9. The process of claim 1, wherein the reaction is performed at 40 to 80° C.

* * * * *